United States Patent
Cordes et al.

(10) Patent No.: US 10,816,627 B2
(45) Date of Patent: Oct. 27, 2020

(54) SYSTEM, METHOD AND COMPUTER PROGRAM FOR MAGNETIC RESONANCE SCANNERS

(71) Applicant: Fraunhofer-Gesellschaft zur Foerderung der angewandten Forschung e.V., Munich (DE)

(72) Inventors: Cristoffer Cordes, Bremen (DE); Thorsten Honroth, Gau-Odernheim (DE); Saulius Archipovas, Bremen (DE); David Porter, Regensburg (DE); Matthias Guenther, Bremen (DE)

(73) Assignee: Fraunhofer-Gesellschaft zur Foerderung der angewandten Forschung e.V., Munich (DE)

( * ) Notice: Subject to any disclaimer, the term of this patent is extended or adjusted under 35 U.S.C. 154(b) by 152 days.

(21) Appl. No.: 16/095,348

(22) PCT Filed: Apr. 20, 2017

(86) PCT No.: PCT/EP2017/059413
§ 371 (c)(1),
(2) Date: Oct. 19, 2018

(87) PCT Pub. No.: WO2017/182579
PCT Pub. Date: Oct. 26, 2017

(65) Prior Publication Data
US 2019/0128983 A1   May 2, 2019

(30) Foreign Application Priority Data
Apr. 20, 2016   (DE) ................ 10 2016 206 720

(51) Int. Cl.
*G01R 33/60* (2006.01)
*G01R 33/54* (2006.01)
(Continued)

(52) U.S. Cl.
CPC ............ *G01R 33/543* (2013.01); *A61B 5/055* (2013.01); *G01R 33/385* (2013.01)

(58) Field of Classification Search
CPC .............. G01R 33/543; G01R 33/5608; G01R 33/4828; G01R 33/3415; G01R 33/385;
(Continued)

(56) References Cited

U.S. PATENT DOCUMENTS

| | | | |
|---|---|---|---|
| 2003/0095150 A1* | 5/2003 | Trevino | G16H 40/20 715/810 |
| 2009/0175524 A1 | 7/2009 | Kachi et al. | |

(Continued)

FOREIGN PATENT DOCUMENTS

| | | |
|---|---|---|
| CN | 104215922 | 12/2014 |
| DE | 102009057582 | 6/2011 |

(Continued)

OTHER PUBLICATIONS

Bernstein et al., "Handbook of MRI Pulse Sequences," Elsevier Academic Press, 2004, 1021 pages.

(Continued)

*Primary Examiner* — Jermele M Hollington
*Assistant Examiner* — Taqi R Nasir
(74) *Attorney, Agent, or Firm* — Ellen M. Bierman; Lowe Graham Jones PLLC

(57) ABSTRACT

The invention relates to a system for providing at least part of a pulse sequence for acquiring imaging information using a magnetic resonance scanner, a corresponding method and a corresponding computer program. The system comprises a sequence module providing unit, wherein one or more sequence modules comprise a hierarchy description and a parameter description, a sequence hierarchy generating unit for generating a sequence hierarchy based on the sequence modules and the hierarchy description, a parameter depen- (Continued)

dency graph generating unit for generating a parameter dependency graph based on the parameter dependencies comprised in the parameter description of the sequence modules. The parameter dependencies are decoupled from the sequence hierarchy. The system, method and computer program of the invention allow for an improved determination of at least part of a pulse sequence.

15 Claims, 6 Drawing Sheets

(51) Int. Cl.
*A61B 5/055* (2006.01)
*G01R 33/385* (2006.01)
(58) Field of Classification Search
CPC .... G01R 33/283; G01R 33/307; G01R 33/60; G01V 3/32; E21B 49/08; E21B 2049/085; G01N 24/10; A61B 5/055
See application file for complete search history.

(56) References Cited

U.S. PATENT DOCUMENTS

| | | | |
|---|---|---|---|
| 2010/0090694 A1* | 4/2010 | Heid | G01R 33/54 324/309 |
| 2013/0249551 A1* | 9/2013 | Kuehn | G01R 33/543 324/309 |
| 2015/0097562 A1* | 4/2015 | Grodzki | G01R 33/543 324/309 |

FOREIGN PATENT DOCUMENTS

| | | |
|---|---|---|
| DE | 102012204625 | 11/2013 |
| EP | 1315115 | 5/2003 |

OTHER PUBLICATIONS

Cordes et al., "Parameter Dependency in Modular MR Sequences using Directed Graphs," Proc. Intl. Soc. Mag. Reson. Med. 24, 2016, 3 pages.
International Search Report and Written Opinion of the International Searching Authority dated Jul. 17, 2017, in International Patent Application No. PCT/EP2017/059413, 11 pages.
Magland et al., "Pulse Sequence Programming in a Dynamic Visual Environment: SequenceTree," Magnetic Resonance in Medicine, 75:257-265 (2016).
Rinck, "Magnetic Resonance in Medicine," The Basic Textbook of the European Magnetic Resonance Forum, Fifth Revised Edition, 2003, 264 pages.
Stoecker et al., "High-performance computing MRI simulations," Magnetic Resonance in Medicine, 2010, 64(1), 186-193.

* cited by examiner

SYSTEM, METHOD AND COMPUTER PROGRAM FOR MAGNETIC RESONANCE SCANNERS

CROSS-REFERENCE TO RELATED APPLICATIONS

This application is a U.S. national phase of International Patent Application No. PCT/EP2017/059413 filed Apr. 20, 2017; which claims priority from Germany Patent Application No. 10 2016 206 720.6 filed Apr. 20, 2016, the contents of which applications are incorporated herein by reference in their entireties.

TECHNICAL FIELD

The invention relates to a system for providing at least part of a pulse sequence for acquiring imaging information using a magnetic resonance scanner, a corresponding method and a corresponding computer program.

SUMMARY

A pulse sequence in the context of magnetic resonance scanners can be defined as the sequence of control instructions for the acquisition of imaging information in the magnetic resonance (MR) scanner. The pulse sequence can comprise one or more radio frequency (RF) pulses to be radiated into the tissue of a subject, together with instructions controlling a magnetic field surrounding the subject, such as a direction, strength and structure (e.g. gradient) thereof. Tomographic images of examined objects can be acquired from the resulting MR signal. A part of the pulse sequences can be a parameter of the pulse sequence, a temporal subrange of the pulse sequence or even the entire pulse sequence. Parameters of the pulse sequence are known in the art and include, for instance, duration or measurement time, total energy, power, and a parameter defined within the scope of the temporal subrange, such as an amplitude, a duration and a shape of gradient and RF pulses, or coil settings for acquisition procedures. Further important physical parameters are a Specific Absorption Rate (SAR) of energy absorbed by the subject, peripheral nerve stimulation (PNS) or parameters related to acoustics such as acoustic resonance effects of the MR scanner.

An overview of MR imaging (MRI) pulse sequences and sequence elements or methods for pulse sequences is given in the "Handbook of MRI Pulse Sequences" by M. Bernstein et al., Elsevier, 2004, for instance, the contents of which are herein entirely incorporated by reference.

It is known to create pulse sequences from multiple sequence blocks or methods, which are high in number and complexity, such that a manual combination and contextual redevelopment of methods requires a large amount of resources in development, methodological expertise and quality assurance. Thus, in developing MRI sequences it is an aim to obtain complex sequence blocks or methods that are flexibly reusable.

Sequence blocks or methods are often assembled to form more complex MRI sequence elements by way of abstraction into a hierarchy of sequence modules. A set of basic elements that correspond to device instructions, i.e. setting a coil voltage, correspond to a low hierarchy of sequence modules. On the other end of the hierarchy, a sequence module representing the full MRI sequence is provided, which directly or indirectly controls one or more other sequence modules, e.g. methods or basic elements, depending on a set of more abstract parameters, called a sequence protocol. MRI sequence and sequence protocol can be used for instantiating the pulse sequence.

Combining sequence blocks or methods is challenging due to the dependency depth of parameters associated with the respective sequence blocks or methods since methods and parameter dependencies, i.e. dependencies necessary for calculating the respective sequence block, are hard to abstract. More precisely, the operator has to know exactly which parameters the respective sequence block or method depends on in order to have that respective parameter readily available at the time of calculating the sequence block.

Expressed differently, sequences follow a hierarchical structure. For instance, basic pulses like a trapezoidal gradient pulse or a sinc-shaped radiofrequency pulse are combined to achieve a slice selection. Then, they are for instance further combined to obtain an excitation module and, can be combined with even further modules such as readout, background suppression, spoiling, loop structure and so on, to an adequate sequence capable of acquiring medical images. A particularity of developing sequences for magnetic resonance therapy is that dependencies among modules cross hierarchical borders frequently. For instance, parameters of a basis pulse of the slice selection and parameters of a basis pulse of the readout directly depend on each other. Accordingly, the main task of developing sequences is to change a deep-rooted concept for another concept while leaving the remainder of the sequence and hierarchy unchanged. However, the new concept can imply completely different connections to or dependencies on other modules which, together with possible side effects, have to be considered and resolved by the sequence developer.

Existing solutions for determining pulse sequences for magnetic resonance imaging mix monolithical and modular definitions of a sequence. Both extremes have significant drawbacks for the development process and a mixture of both concepts shares the drawbacks of both concepts.

In a monolithical concept, all dependencies are collected and organized at a central location. With this solution, a sequence developer can directly employ structural changes even over multiple hierarchical layers, since all dependencies are explicitly known at the central location. However, parameter dependencies are not logically encapsulated or can be bundled, so that a sequency developer has to understand the entire sequence to be able to exchange one concept for another, while he/she has to have an overview of all possible side effects which can result from parameter dependencies. In practice, this generally corresponds to a complete redevelopment of the entire sequence. Parts of the definition of the sequence will not be able to be reused, since, according to the monolithical concept, they cannot be separated from other parts of the sequence definition.

On the other side, in a modular concept, parameter dependencies that cross hierarchical layers are not allowed, since they would impede the reusability of the modules. For instance, in case a new dependency over multiple layers is needed, each intermediate sequence object, for instance each module in a tree structure hierarchy of sequence modules, has to be adapted in order to support the new dependency. Accordingly, in order to apply structural changes, a significant amount of the modules is to be adapted, which also is a very complex and laborious task. Nevertheless, an advantage of the modular concept is the ability to reuse parts, i.e. modules, in case they are used in an identical form, and thus no redevelopment of the entire part as in the monolithical concept would be necessary.

From DE 10 2012 204 625 B4 it is known, in order to determine a complete parameter of a pulse sequence comprised of multiple pulse sequence modules, to electronically store parameter information of pulse sequence modules that comprise a pulse sequence configured to operate a magnetic resonance apparatus in leaves and nodes of a tree structure, and, by means of a processor, to access and retrieve the parameter information stored in said tree structure and to execute a tree structure evaluation algorithm to determine the complete parameter.

Unfavourable of this solution is that parameter dependencies of the sequence modules comprised in the tree structure have to be exactly known prior to calculation. The parameter dependencies either have to be explicitly defined within each module, or the modules, more precisely the parameter dependencies of each module, have to be adapted in case of structural modifications to the tree structure. This highly limits the versatility of complex sequence modules since structural changes to the sequence structure require a high expertise and excessive work for every single adaptation. Further, it increases the likelihood of errors and mistakes due to the high number and complexity depth of the parameters the modules depend on. Finally, a health risk for a patient arises in case non-optimal or erroneous pulse sequences are applied that lead to more than necessary energy or treatment duration.

From DE 10 2009 057 582 A1 a method to configure at least one partial range of pulse sequence for operating a magnetic resonance device is known, wherein the pulse sequence is composed of at least two different program units, wherein information and/or at least one parameter is exchanged between the individual program units by a computerized mediator unit.

Unfavorable of this solution is, that the orchestration of parameter exchanges is tightly coupled to the individual program units or a centralized location. This yields all problems of modular and monolithical concepts respectively. Structural changes and reusability are still hindered depending on the degree of modularity.

Frameworks or systems for providing or developing pulse sequences are generally developed with the aim to control or instruct the hardware of the magnetic resonance scanner, i.e. implement the logical structure imposed by the hardware, such that the magnetic resonance scanner can easily be driven based on the developed pulse sequences. However, interconnections between modules, i.e. logic included in the pulse sequence itself, are difficult to be reproduced by hardware instructions, are thus not enabled by known frameworks or systems, which eventually renders sequence development a complex, laborious and error-prone task.

SUMMARY

It has thus been an object of the present application to provide a system, a method and a computer program of the type indicated above, which allow for an improved determination of at least part of a pulse sequence.

In a first aspect, a system for providing at least part of a pulse sequence for acquiring imaging information using a magnetic resonance scanner is provided. The system comprises: a sequence module providing unit for providing sequence modules, wherein one or more sequence modules comprise a hierarchy description arranged for comprising one or more hierarchically subordinated sequence modules, and/or a parameter description arranged for comprising one or more parameter dependencies; a sequence hierarchy generating unit for generating a sequence hierarchy based on the sequence modules and the hierarchy description; a parameter dependency graph generating unit for generating a parameter dependency graph based on the parameter dependencies comprised in the parameter description of the sequence modules and based on the sequence hierarchy; and a parameter determination unit for determining a parameter of the pulse sequence based on at least part of the parameter dependency graph.

DETAILED DESCRIPTION

Figure 1:
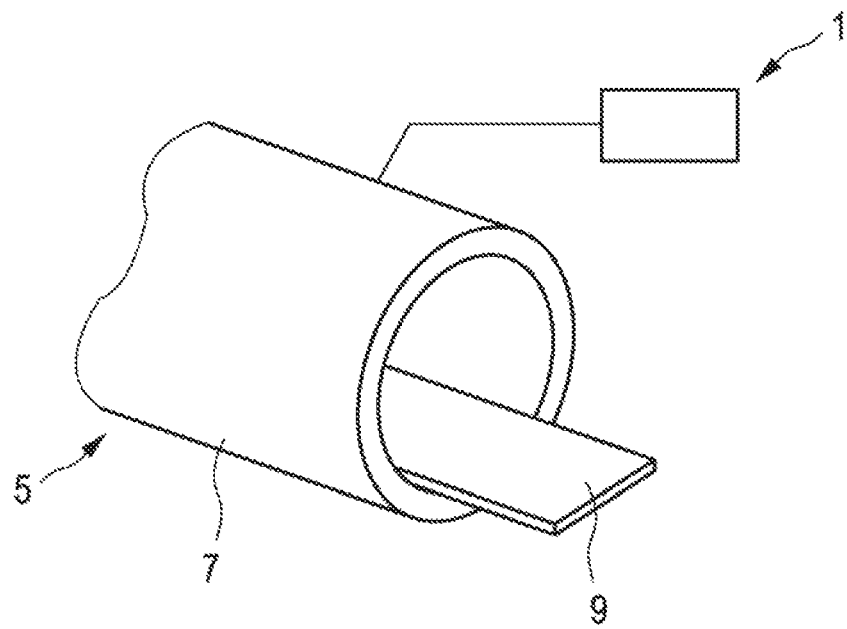
FIG. 1 schematically and exemplarily shows a magnetic resonance (MR) scanner.

In a first aspect, a system for providing at least part of a pulse sequence for acquiring imaging information using a magnetic resonance scanner is provided. The system comprises: a sequence module providing unit for providing sequence modules, wherein one or more sequence modules comprise a hierarchy description arranged for comprising one or more hierarchically subordinated sequence modules, and/or a parameter description arranged for comprising one or more parameter dependencies; a sequence hierarchy generating unit for generating a sequence hierarchy based on the sequence modules and the hierarchy description; a parameter dependency graph generating unit for generating a parameter dependency graph based on the parameter dependencies comprised in the parameter description of the sequence modules and based on the sequence hierarchy; and a parameter determination unit for determining a parameter of the pulse sequence based on at least part of the parameter dependency graph.

Preferentially, the explicit determination of parameters, i.e. calculation instructions necessary for determining a parameter, do not have to be provided by a sequence developer, who intends to develop a pulse sequence, but are determined by the system according to the invention based on the generated parameter dependency graph. Expressed differently, calculations do not have to be specified directly by the user, but are generated based on the generated parameter dependency graph which represents the structure of the dependencies between the parameters. Decoupled therefrom, the system generates a sequence hierarchy of the sequence modules, which is comparable to the sequence hierarchies as known in the art. However, since the parameter dependency graph is decoupled from the hierarchy, calculations necessary for determining the parameters do not have to be specified by the user and allow for more efficient calculations and at the same time for an easier and less error-prone programming or development of a sequence by the sequence developer.

Further preferentially and expressed even differently, the sequence developer can define rules the sequence has to follow, for instance, a line acquisition loop scheme, a particular encoding or a particular excitation. Based on these rules the sequence has to follow, two decoupled structures, represented by graphs, are determined. These are, for instance, a known module sequence hierarchy and a parameter dependency graph, which is decoupled therefrom. The parameter dependency graph provides a clearly defined and easy to understand structure based on nodes and edges interconnecting the nodes. Calculations for determining the parameters are not bound to modules, a way or path between source parameters and goal parameters, i.e. the steps or calculations necessary for determining a parameter, is directly obtainable by following the parameter dependency graph and can thus be separated from calculations which are irrelevant to the goal parameter. Further, since the parameter dependency graph allows a separation of relevant and irrelevant calculations for determining a parameter, a more efficient determination of a parameter of the pulse sequence can be achieved.

Finally, since the structure of the parameter dependencies, i.e. as represented in the parameter dependency graph, is easy to recognize, an implementation of an execution of prepared pulse sequences on hardware can easily be implemented. Moreover, also a graphical understanding of the calculations for the user can be supported.

Since the parameter determination unit determines a parameter of the pulse sequence based on at least part of the parameter dependency graph, and since the parameter dependency graph is based on the parameter dependencies and based on the sequence hierarchy, the parameter determination unit can determine the parameter of the pulse sequence directly from the parameter dependency graph without having to consider either a part of or the entire sequence hierarchy. Advantageously, a parameter of the pulse sequence, such as the specific absorption rate (SAR) of energy of the subject, can be determined in a more efficient and more accurate way. Thereby, a parameter optimization leading to a minimization of the energy impact onto the subject can be performed.

Since the parameter dependency graph generating unit generates the parameter dependency graph based on the sequence hierarchy, the parameter dependencies do not have to follow a predefined succession or order. Thus, it is advantageously possible to reuse sequence modules in another sequence hierarchy or order without having to perform corrections or updates to the parameter dependencies comprised in the parameter description of the respective modules. In other words, sequence modules can comprise parameter dependencies which are always valid regardless of the particular order of the sequence modules in the sequence hierarchy. This is of particular advantage in complex sequences, in which many parameter dependencies of various sequence modules can be interwoven, crossing hierarchical barriers.

Based on the parameter dependency graph, an improved determination method can be implemented by the parameter determination unit for determining a particular parameter of the pulse sequence. The parameter can, for instance, be a complete parameter of the pulse sequence, wherein a complete parameter is a physical parameter that characterizes the pulse sequence as a whole. For example, the complete parameter can be a total energy of the pulse sequence, a total duration of the pulse sequence, an absorbed energy, i.e. the SAR over time, a maximum PNS, acoustic resonance effects of the MR scanner or any other technical/physical parameter that can be determined from the pulse sequence. By determining the parameter based on the parameter dependency graph, unphysical or unfeasible parameters can be determined in an efficient way.

For instance, parameters of the pulse sequence are configured by an operator of the scanner. Parameters set or defined by an operator can have an influence on the pulse sequence as a whole and on other parameters of the pulse sequence. It is of importance that information about physically or logically impractical parameters be provided. In other words, the aim can be to check a parameter value range for valid and invalid intervals that are the result of calculations specific to the pulse sequence. For instance, an operator can introduce apparently feasible parameters, which due to complex dependencies result in other parameters to be impractical, such as a duration of a physical pulse to be smaller than zero.

In this embodiment, one or more sequence modules comprise a hierarchy description and a parameter description. However, in this or further embodiments, one or more sequence modules can comprise only the hierarchy description and one or more sequence modules can comprise only the parameter description.

Since the parameter dependencies are decoupled from the sequence hierarchy, sequence modules can be used in various contexts without having to adapt the respective parameter dependencies. Accordingly, the investigation and development of new, physically advantageous pulse sequences is facilitated.

In an embodiment, the system further comprises a pulse sequence instantiation unit for instantiating at least part of the pulse sequence based on at least part of the parameter dependency graph and at least part of the sequence hierarchy.

For instance, the pulse sequence instantiation unit firstly calculates parameters that have been resolved based on the parameter dependency graph and then uses the sequence hierarchy to instantiate at least part of the pulse sequence based on the calculated parameters based on the resolved parameter dependencies, and based on the sequence hierarchy provided by the sequence hierarchy generating unit. In other words, since the parameter dependencies are decoupled from the sequence hierarchy, structure elements, i.e. sequence modules, of the pulse sequence can be exchanged easily, without implying adaptations to the parameter dependencies.

In an embodiment of the system, the hierarchy description of one or more sequence modules is further arranged for comprising at least one structural operation description for defining a structural operation on the sequence hierarchy, wherein the sequence hierarchy generating unit is arranged for generating the sequence hierarchy further based on the at least one structural operation description in the sequence module.

For instance, a structural operation on the sequence hierarchy, which is defined in one or more sequence modules, can be a copy and/or clone operation, which copies/clones one sequence module to a particular position within the sequence hierarchy. This allows, for instance and without being limited, optimization methods to be implemented within the pulse sequence or modules to be reutilized at various positions within the pulse sequence. It is preferred that the structural operation be context aware such that a context, for instance parameter dependencies and hierarchical connections, within the sequence hierarchy is considered upon performing the structural operation.

In an embodiment of the system, the hierarchy description is arranged for comprising hierarchically directly subordinated sequence modules and/or hierarchically subordinated sequence modules with one or more hierarchically intermediate sequence modules.

In this example, hierarchically subordinated sequence modules which are directly subordinated explicitly define other sequence modules over one hierarchical layer. For instance, such hierarchy description may describe a timing scheme that has directly subordinated preparation, excitation and read-out sequence modules. In another example, hierarchically subordinated sequence modules are subordinated with intermediate sequence modules and can be explicitly defined over multiple hierarchical layers. For instance, the hierarchy description of a sequence module may describe that a subordinated sequence module used for excitation should use a specific pulse, without defining the excitation sequence module explicitly.

In an embodiment of the system, the sequence module is arranged to define at least one hierarchically subordinated sequence module or a parameter dependency implicitly. An implicit definition is used as an implied definition by reference to another sequence module or parameter without explicitly defining the reference.

In this embodiment, the sequence module relies on sequence element properties that it does not provide itself. The missing hierarchical elements or nodes of the parameter dependency graph need to be provided elsewhere during the sequence hierarchy and parameter dependency graph generating processes, e.g. by another sequence module comprising a different sequence element description, to allow for well-defined structures.

In an embodiment of the system, the sequence module is further arranged to comprise an identifier for at least one of the hierarchically subordinated sequence modules in the hierarchy description.

One or more sequence modules can be instantiated in more than one instance within the pulse sequence. In order to distinguish the more than one instances of the same sequence module, an identifier, such as a name for the sequence module, can be used. In other words, parameter dependency inconsistencies among subordinated sequence modules can be avoided.

In an embodiment of the system, the sequence module is further arranged to comprise calculation instructions as part of the parameter description. Calculation instructions implement the actual method or sequence, such as including instructions for operating a MR scanner. In one example, a trapezoidal gradient pulse can be defined through its start time, integral, duration and the condition to rise to the system-wide maximum amplitude at a certain percentage of the system capabilities. Based on these parameters, an adequate set of calculations can be realized as parameter graph dependencies that result in the start time, ramp times, the plateau time and the amplitude of the pulse, uniquely defining the sequence element as one or more system instructions for operating the MR scanner. Clearly, other examples of sequence modules and calculation instructions are contemplated.

In an embodiment of the system, the sequence hierarchy generating unit is arranged for generating the sequence hierarchy based on the sequence modules and the respectively comprised hierarchically subordinated sequence modules of the hierarchy description. More precisely, the sequence hierarchy generating unit generates the overall sequence hierarchy by considering hierarchically subordinated sequence modules comprised in the hierarchy description of respective sequence modules and arranging the subordinated sequence modules at a lower hierarchy than the sequence module that comprises the hierarchically subordinated sequence modules. Hierarchically subordinated sequence modules can be directly subordinated, implicitly defined or subordinated over multiple hierarchical layers as detailed above. Further, the sequence hierarchy generating unit can in some embodiments consider structural operations comprised within one or more sequence modules for performing structural operations on the sequence structure.

In an embodiment of the system, the pulse sequence instantiation unit is arranged for combining the sequence hierarchy and the parameter dependency graph to a sequence parameter graph and for determining parameters from the resolved parameter dependencies within the sequence parameter graph. Thereby, a parameter of the pulse sequence can advantageously not be determined as a property of the respectively associated sequence module but as part of the sequence parameter graph which is global for the entire pulse sequence.

In an embodiment of the system, the sequence hierarchy generating unit is arranged to provide the sequence hierarchy as a directed tree structure and/or the parameter dependency graph generating unit is arranged to provide the parameter dependencies graph as a directed acyclic graph. Evaluation and manipulation of parameters represented as a directed acyclic graph is beneficial in terms of processing and causal relations, e.g. it is sufficient to evaluate successor elements in an acyclic graph in case a parameter changes instead of re-evaluating the entire parameter graph or even the entire pulse sequence.

In a further aspect, a method for determining at least part of a pulse sequence for acquiring imaging information using a magnetic resonance scanner is provided. The method comprises: providing sequence modules, wherein one or more sequence modules comprise a hierarchy description arranged for comprising one or more hierarchically subordinated sequence modules, and/or a parameter description arranged for comprising one or more parameter dependencies; generating a sequence hierarchy based on the sequence modules and the hierarchy description; generating a parameter dependency graph based on the parameter dependencies comprised in the parameter description of the sequence modules; and determining a at least part of the pulse sequence based on at least part of the parameter dependency graph. Preferably, at least part of the pulse sequence is a parameter of the pulse sequence.

In an embodiment of the method, the method further comprises instantiating at least part of the pulse sequence based on the parameter dependency graph and the sequence hierarchy.

In an embodiment of the method, the sequence hierarchy is represented as a directed tree structure and the parameter dependencies graph is represented as a directed acyclic graph.

In a further aspect, a computer program for determining at least part of a pulse sequence for acquiring imaging information using a magnetic resonance scanner is provided. The computer program comprises program code means for causing a system as defined in claim 1 to carry out the method as defined in claim 11, when the computer program is run on the system.

In a further aspect, a computer program for driving or simulating a magnetic resonance scanner is provided. The computer program comprises program code means for causing a magnetic resonance scanner, or a simulation of a magnetic resonance scanner, to execute at least part of a pulse sequence for acquiring imaging information by carrying out the steps of: i) receiving a sequence hierarchy comprising one or more sequence modules, wherein the sequence modules comprise a hierarchy description arranged for comprising one or more hierarchically subordinated sequence modules, and a parameter description arranged for comprising one or more parameter dependencies, ii) receiving a parameter dependency graph comprising parameters of the pulse sequence connected by parameter dependencies, and iii) executing at least part of the pulse sequence by calculating a parameter of the pulse sequence based on the parameter dependency graph.

Since the parameter dependency graph is decoupled from the sequence hierarchy, a logic for calculating or determining the parameters of the pulse sequence does not have to be explicitly provided in the sequence modules or the sequence hierarchy but can be determined based on the parameter descriptions and the parameter dependency graph alone. This allows reusability of the sequence modules in different structures without the need to provide adaptations to several sequence modules, since even if parameter dependencies cross hierarchical borders, the dependencies between parameters and the required order of calculations are determined by the parameter dependency graph which is decoupled from the sequence hierarchy.

For this reason, even if parameter dependencies cross hierarchical boundaries, the at least part of the pulse sequence can easily be determined by traversing the sequence hierarchy and the parameter dependency graph, which is decoupled from the sequence hierarchy. Accordingly, a straightforward implementation of the computer program for driving or simulating a magnetic resonance scanner even on different types of magnetic resonance scanners is facilitated.

It shall be understood that the system for determining at least part of a pulse sequence for acquiring imaging information using a magnetic resonance scanner of claim 1, the method for determining at least part of a pulse sequence for acquiring imaging information using a magnetic resonance scanner of claim 11 and the computer program for determining at least part of a pulse sequence for acquiring imaging information using a magnetic resonance scanner of claim 14 have similar and/or identical preferred embodiments, in particular, as defined in the dependent claims.

It shall be understood that a preferred embodiment of the present invention can also be any combination of the dependent claims or above embodiments with the respective independent claim.

These and other aspects of the invention will be apparent from and elucidated with reference to the embodiments described hereinafter.

FIG. 1 schematically and exemplarily shows a magnetic resonance (MR) scanner 5 which receives input from a determination system 1 according to the invention, which is described in more detail with reference to FIG. 2. Different pulse sequences are effectuated and executed in the examination of a subject in the MR scanner 5. MR scanner 5 consists of the actual scanner 7, which comprises at least a magnet (not shown), a gradient magnetic field source such as gradient coils (not shown), a radio frequency (RF) source such as a RF coil (not shown), and a RF reception coil for receiving the MR response (not shown). Determination system 1 is arranged for determining at least part of a pulse sequence for acquiring imaging information using MR scanner 5. In this respect, it is referred for instance to the contents of Rinck P. "Magnetic Resonance in Medicine. The Basic Textbook of the European Magnetic Resonance Forum. 9th edition; 2016.", Electronic version 9, published 1 Mar. 2016, which is hereby entirely incorporated by reference herein.

Figure 2:
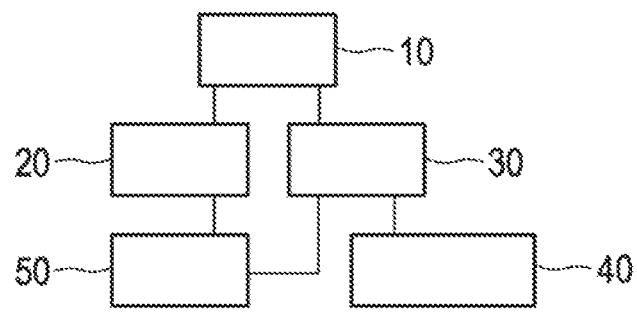
FIG. 2 schematically and exemplarily shows a system for determining at least part of a pulse sequence for acquiring imaging information using a magnetic resonance scanner according to the invention.
Figure 2:

FIG. 2 shows schematically and exemplarily determination system 1, which comprises a sequence module providing unit 10, a sequence hierarchy generating unit 20, a parameter dependency graph generating unit 30, a parameter determination unit 40 and a pulse sequence instantiation unit 50.

Sequence module providing unit 10 is arranged for providing sequence modules. Sequence modules comprise a hierarchy description, which is arranged for comprising one or more hierarchically subordinated sequence modules. Additionally, or alternatively, a sequence module comprises a parameter description arranged for comprising one or more parameter dependencies. Further, sequence modules can comprise at least one structural operation description, which describes a structural operation on the sequence hierarchy. Together with the parameter description, the sequence module can comprise parameter calculation instructions, which eventually operate the MR scanner after being instantiated and inputted to the scanner. Examples of structure modules used in the prior art are provided in FIGS. 3a to 3d. Practical examples of sequence modules provided by sequence module providing unit 10 are then given in FIGS. 4 to 9.

Sequence hierarchy generating unit 20 generates a sequence hierarchy based on the sequence modules provided by sequence module providing unit 10 and the hierarchy description contained within one or more sequence modules out of the provided sequence modules. In this example, sequence hierarchy generating unit 20 generates the sequence hierarchy as a tree-structure comprising the sequence modules as leaves and nodes of a tree-structure. Sequence modules without hierarchically subordinated sequence modules could be represented by leaves, wherein sequence modules comprising one or more hierarchically subordinated sequence modules can be represented as nodes having links to the respectively subordinated sequence modules. The hierarchy description can comprise explicitly defined subordinate modules, over either one or multiple hierarchical layers or an implicit/clone definition of subordinated modules, which could, for instance, be resolved by structural operations on the sequence hierarchy.

Parameter dependency graph generating unit 30 generates a parameter dependency graph based on the parameter dependencies comprised in the parameter description of the sequence modules. Parameter dependencies express how target parameters depend on other parameters. Since parameter dependency graph generating unit 30 generates the parameter dependency graph which is independent from the sequence hierarchy, i.e. parameter dependency is decoupled from sequence hierarchy, input parameters do not have to be predefined in the description or sequence modules provided by sequence module providing unit 10. Further, it is not necessary that the target parameter be associated with the sequence module defining it. For instance, a pulse being an example of a sequence module on a low hierarchical layer can comprise the flip angle as a parameter it is dependent on. This parameter, the flip angle, can be defined through a protocol parameter, which would correspond to a parameter property of a high hierarchical layer. Further, this parameter, or more precisely the parameter's dependency, does not necessarily have to be defined at the high hierarchical layer, but can instead be defined in an intermediate hierarchical layer. A resulting advantage is that responsibilities of a module can be separated by their function and thus be reused. At the same time, structural changes to the sequence structures through multiple hierarchical layers become possible without the need to manipulate the definition of intermediate sequence modules.

In other words, a sequence module can provide an abstract strategy to describe certain parameters that are relevant to the pulse sequence. In this invention, the module does not need to provide a fully self-contained set of operations, but can be left incomplete to allow other sequence modules to influence this strategy. This way, a sequence module can be more versatile. Without the added context given by the other sequence modules, parameter calculations are not well-defined when sequence modules are not self-contained. For this reason, parameter dependency graph determination unit 30 is required to resolve the parameter dependencies of the whole sequence in a more comprehensive manner to yield the parameter graph structure.

Parameter determination unit 40 determines a parameter of the pulse sequence based on at least part of the parameter dependency graph. Since parameter determination unit 40 just relies on the parameter dependency graph for the determination of a parameter, the parameter can be determined in an efficient way, without carrying out unnecessary calculations or investigation on possible interactions between parameters. Parameter determination unit 40 can thus determine information about physically or logically impractical parameters, which allows to check a parameter segment for valid and invalid subsegments, which would be the result of pulse sequence specific calculations.

Pulse sequence instantiation unit 50 instantiates at least part of the pulse sequence based on at least part of the parameter dependency graph and at least part of the sequence hierarchy. Modularity and connectivity of logical structure elements within MRI sequences is non-trivial and non-compatible with a strict hierarchy in its theoretical nature. Since modules are not defined directly, but implicitly, the connection of structural elements is part of the sequence module description. By allowing open definitions and the resulting possibilities of modularized structure definitions of sequence modules, the development process of developing pulse sequences is simplified to only defining differences. This way, pulse sequences can be developed further without having to duplicate a preparation routine with complex structural connections.

FIGS. 3a to 3d schematically and exemplarily illustrate deficiencies of sequence modules defining pulse sequences known in the art. It is known to assemble multiple MRI sequence elements or sequence modules to form more complex sequence elements that eventually lead to the pulse sequence. The foundation of this process, i.e. sequence modules at the lowest hierarchy, is a set of basic elements that correspond to device instructions such as setting a coil voltage. The topmost level of abstraction, i.e. the sequence module at the highest hierarchy, is the full MRI pulse sequence, which ultimately controls those basic sequence modules depending on a set of more abstract parameters, called sequence protocol.

Figure 3A:
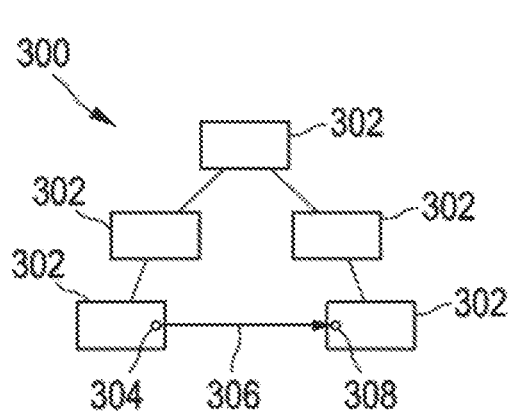
FIG. 3a-3d schematically and exemplarily illustrate deficiencies of pulse sequences known in the art.

FIG. 3a shows an example of a monolithically defined sequence 300, i.e. a self-contained sequence which is defined without modularity. The hierarchy of sequence 300 comprising five sequence elements 302 is configured from outside and assembled manually for each sequence. A required calculation 306 between two parameters 304 and 308 of two sequence elements 302 is specified manually.

This way, modules and calculation routines can be exchanged regardless of their hierarchical relation. However, the high amount of responsibility of this configuration from outside antagonizes modularization.

Figure 3B:
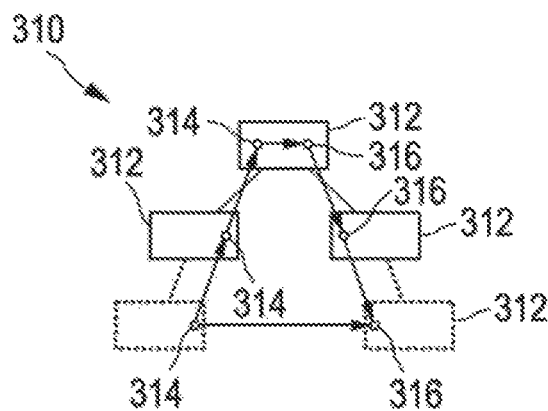

FIG. 3b illustrates modular sequence hierarchy 310, in which sequence elements 312 are highly modularized. There is no information exchange beyond multiple hierarchical layers and each sequence module 312 has the responsibility to configure its directly subordinated hierarchy only. As compared to the monolithical configuration in FIG. 3a, a parameter dependency between parameter 314 and 316, i.e. a calculation dependency that crosses hierarchical boundaries, needs to be passed through each intermediate layer. Accordingly, structural changes in lower hierarchical layers would require manipulation of all intermediate modules.

Figure 3C:
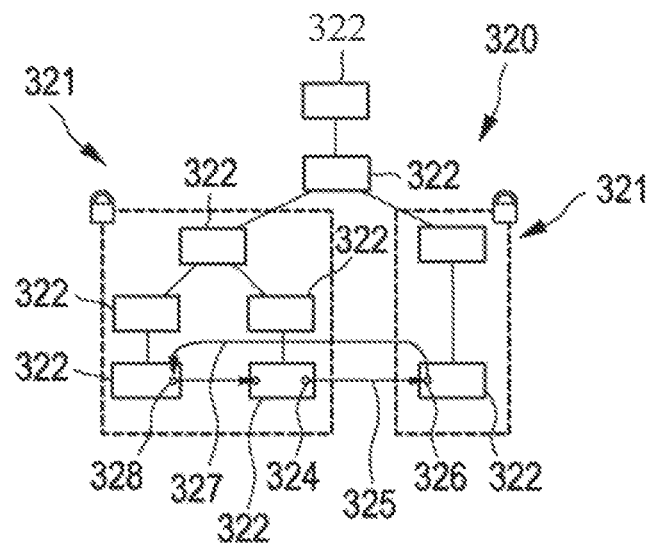
Figure 3D:
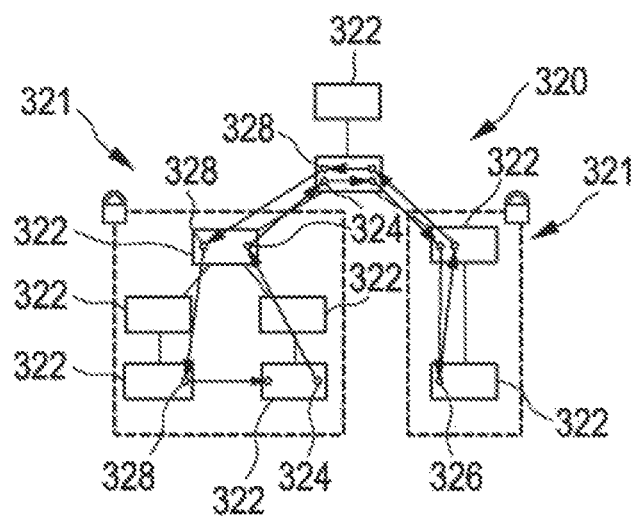

Both strategies can be combined, as illustrated in FIG. 3c. FIG. 3c illustrates a sequence hierarchy 320, comprising multiple sequence modules 322, which combines two self-contained modularized methods 321. Each of the methods 321 requires parameters 324, 326, 328 from the other module, which were not provided in their original implementation, since they are only relevant to this specific combination. The dependencies are indicated with lines 325 and 327 connecting the modularized methods 321. However, the dependencies 325 and 327 are not feasible, since they cross a hierarchical boundary. In this scenario, both methods 321 need to be adapted in the way shown in FIG. 3d to make the newly required parameters 324, 326 and 328 available. The modularization hinders the structural change. That way, logical independent methods 321 are not autonomously reusable.

Figure 4A:
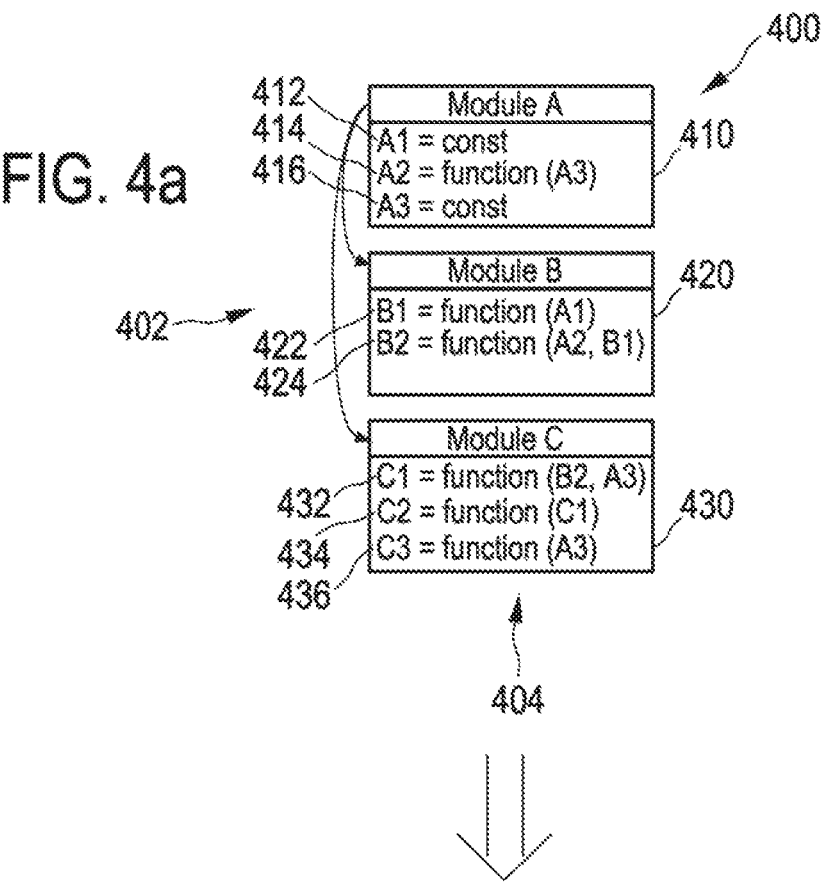
FIG. 4a, 4b schematically and exemplarily illustrate sequence modules and resulting sequence and parameter dependency structures for the determination system of the present invention.

FIG. 4a illustrates a sequence description 400 comprising three sequence modules 410, 420 and 430. The sequence description comprises a hierarchy description 402 and a parameter description 404. Parameter description 404 of module 410 comprises three parameters 412, 414 and 416. Parameters 412 and 416 in this example are constant values, wherein parameter 414 depends on parameter 416. Module 410 has modules 420 and 430 as directly subordinated sequence modules.

Sequence module 420 comprises parameters 422 and 424. Parameter 422 depends on parameter 412 and parameter 424 depends on parameter 422 and 414. In other words, parameter 424 has dependencies on parameters of the same module, namely parameter 422, and of another module, namely parameter 414.

Also, sequence module 430 comprises parameter dependencies, namely parameter 432, which depends on parameters 424 and 416, i.e. parameters of modules 410 and 420, parameter 434, which only depends on parameter 432, and parameter 436, which depends on parameter 416.

Figure 4B:
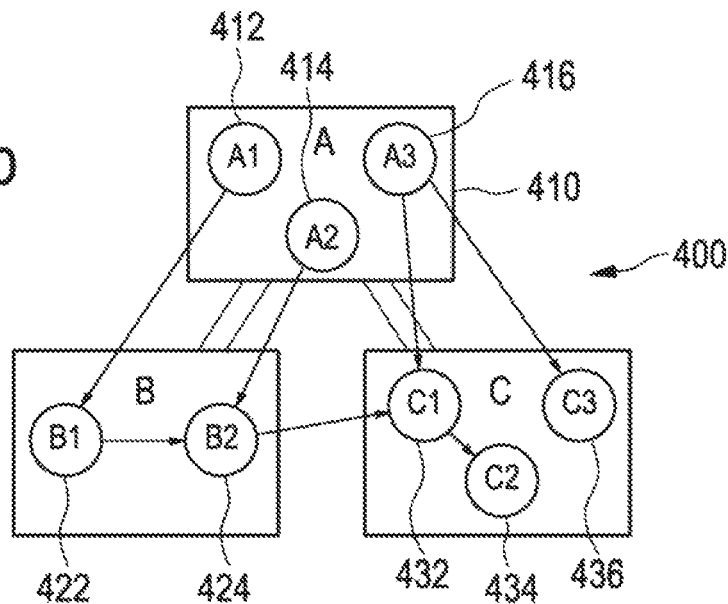

Based on the module descriptions shown in FIG. 4a, objects are instantiated that follow two data structures to realize parameter dependencies and hierarchical dependencies. In FIG. 4b, sequence description 400 is represented by a directed tree showing module 410 on the top and the hierarchically subordinated modules 420 and 430 below. Further, a directed acyclic graph representing the parameter dependencies is overlaid over the directed tree, such that the parameters are part of a sequence global parameter graph and can be viewed linked to the modules that they are associated with. In other and more general words, sequence description 400 is translated to the prepared sequence by assembling the partially implicit hierarchical properties and the completely implicit parameter dependencies to explicit connections of the directed tree and the acyclic graph. The resulting acyclic graph structure of the parameters allows simplifications that cannot be realized by imperative calculation instructions.

In this example, sequence description 400 possesses a logic that can be utilized to simplify and accelerate parameter calculations and the development process. The parameters are embedded into a global data structure that makes side-effects and relevance of parameters accessible and enables the potential for more versatile algorithms and parameter operations for the pulse sequence. The resulting data structures are complex because they contain the cumulative complexity of all modules 410, 420, 430 that define sequence description 400. Therefore, it cannot be expected from a sequence developer to interact or manipulate this structure directly. It is the result of the implicit module descriptions and should only be manipulated through those. Modules 410, 420, 430 can be flexibly reused, because depending on the context, dependencies of subordinated modules at any layer can be injected and reassembled differently to yield the desired result. For example, a phase encoding gradient can be configured to run with a maximal amplitude during dummy cycles but have its amplitude defined through the row index during the actual measurement. In this example, depending parameters, such as the rewinder gradient, stay consistent in both contexts if they are defined depending on the phase encoding gradient amplitude, for instance.

The implicit configuration is enabled by the decoupling of parameter calculation procedures 404 from module hierarchy 402. In the instantiation step, the partially implicit structural definitions and parameter dependencies are assembled to yield the context- and application-specific sequence hierarchy and parameter dependency graph. Parameters are not calculated, saved and manipulated as part of its associated sequence module, but are instead part of the sequence-global parameter graph. In summary, calculation and manipulation of parameters can be achieved independent of sequence hierarchy and calculation operations can be reduced.

Figure 5A:
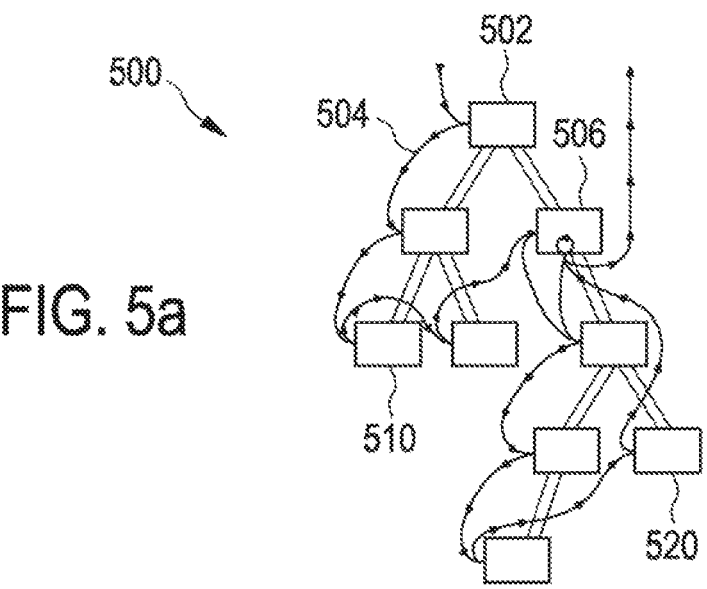
FIG. 5a-5c schematically and exemplarily illustrate operations on a structure according to the invention.

FIG. 5a illustrates a tree-structure of a sequence hierarchy 500, in which a traversal operation is performed. Traversal 504 starts at sequence module 502 at the top of the hierarchy and follows its way along the tree-structure. Various sequence modules 510 are traversed in this example until the traversal arrives at a loop module 506. Loop module 506 indicates repetitions over the subordinated modules including a basic module 520. In this example, also further algorithms can be performed on sequence hierarchy 500 instead of traversal 504, such as a depth search and a width search. A depth search is an uninformed search that searches deeper and deeper into the hierarchy, starting at sequence module 502 and expanding the respective first of the subordinated sequence modules or follow-up nodes. A width search is an uninformed search that searches the width of sequence hierarchy 500 for a sequence module, starting from sequence module 502 and expanding individual hierarchy levels of sequence hierarchy 500.

Figure 5B:
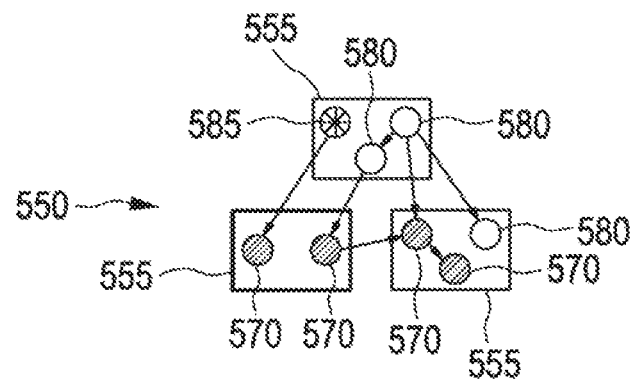

FIG. 5b illustrates a parameter dependency graph 550 of three sequence modules 555. Various parameters indicated as circles within the sequence modules 555 are connected with edges, representing dependencies. In FIG. 5b, a manipulation operation is performed on parameter 560. This manipulation operation leads to an invalidation of all dependent parameters 570, which will be reevaluated directly or upon request after parameter 560 has been manipulated. The execution of calculation operations can be necessary for reevaluating parameters 570 in some examples. Remaining parameters 580 are not dependent on parameter 560 and thus do not have to be reevaluated.

Figure 5C:
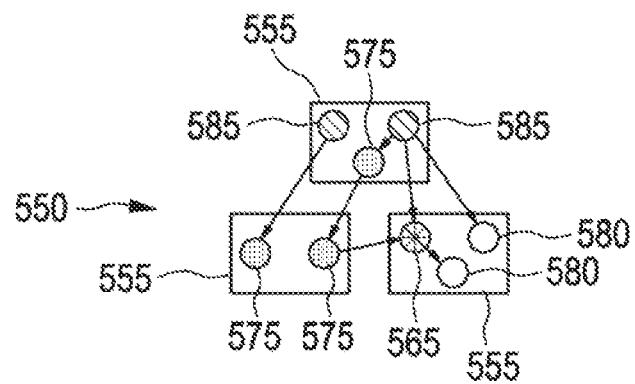

FIG. 5c indicates the same parameter dependency graph 550 as FIG. 5b, wherein a calculation operation is performed on parameter 565. In order to determine parameter 565, all parameters 575 and 585, from which parameter 565 depends, have to be evaluated as well. In this example, parameters 585 are already valid and evaluated and thus can directly be considered. Parameters 575 are tagged as invalid and have to be evaluated in order to become valid prior to the determination of parameter 565.

Generally, execution of the pulse sequence on hardware, i.e. a magnetic resonance scanner, corresponds to a traversal 504 of the sequence structure tree and corresponding execution of the calculation instructions. In previous systems for determining pulse sequences, the calculation instructions are included in sequence modules 502, i.e. the nodes of the tree structure themselves. In this case, it is a task of the user to ensure that calculations in hierarchically lower parts of the sequence are implemented correctly and in the right order. In contrast thereto, the system according to the invention allows for the user to leave the determination of the order of calculations to the system, since this complexity is represented within the parameter dependency graph structure. Accordingly, the logic of executing the sequence is indeed limited to traversing the tree structure and setting and/or getting a parameter of parameter dependency graph 550 at certain points of traversal. For instance, examples of "setting" of parameters can be parameters which are adjusted by an operator of the MRI scanner at an operating terminal or adjusting loop count parameters during execution, which correspond to the acquisition of a particular image line. As an example of a "getting" of parameters, for instance of properties of a trapezoidal gradient pulse, a safety relevant parameter or the overall time of the pulse sequence can be given.

The basic module 520 can then include instructions for directly operating the hardware, i.e. the magnetic resonance scanner.

Further to the advantageous concept of facilitating calculation procedures, a sequence module can dictate structure operations, which concern or act on the sequence structure itself.

Examples of structure operations will be discussed with reference to FIGS. 6 to 9.

Figure 6:
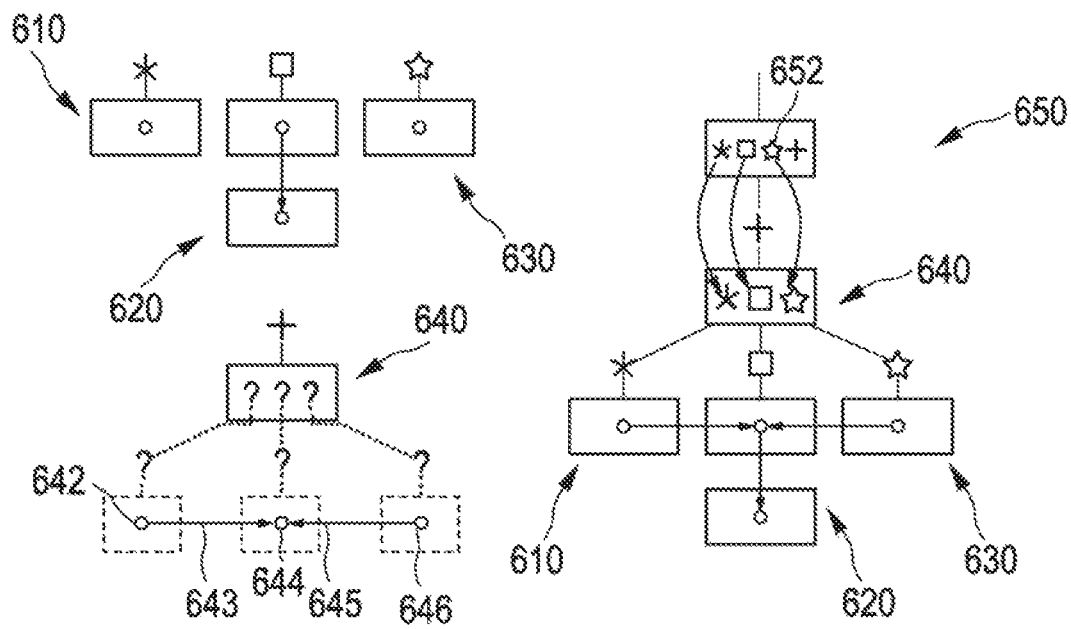
FIG. 6 schematically and exemplarily illustrates a structure hierarchy employing structure abstraction.

FIG. 6 illustrates an example for structure abstraction, which is enabled by the sequence modules of the present invention. An abstract preparation module 610, an excitation module 620 and a read-out module 630 are provided. In many applications, it is desired to combine an excitation structure, a preparation and a read-out, in a versatile way. For this purpose, a structure sequence module 640 is defined, which includes three hierarchically subordinated sequence modules 642, 644 and 646, which are implicitly defined with parameter connections 643 and 645 between these subordinated sequence modules. However, the actual components to be used as sequence module 642, 644 and 646 are not defined at that time. In an actual sequence structure 650, a root sequence module 652 defines to use the abstract sequence module 640 and defines the explicit sequence modules 610, 620 and 630 to be inserted in sequence module 640. From these structure operations, the actual sequence structure 650 is defined.

Figure 7:
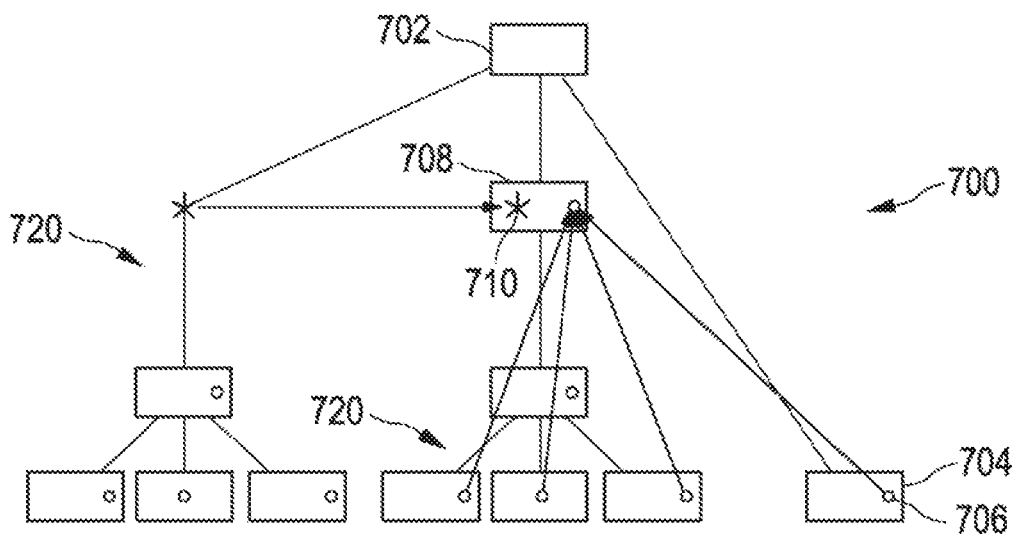
FIG. 7 schematically and exemplarily illustrates a structure hierarchy for abstract parameter determination.

FIG. 7 schematically and exemplarily shows an example of a sequence structure 700 implementing a structure and module dependent parameter calculation. A root sequence module 702 defines a compensating sequence module 704 and a calculation sequence module 708 as hierarchically subordinated sequence modules. In this example, compensating sequence module 704 is directed to refocus the signal to negate the T2* decay and comprises a parameter dependency 706, which depends on the actual pulse sequence. However, the compensation module can be described independent of the sequence and just depends on a resulting parameter, indicated as parameter 706. For this reason, calculation sequence module 708 comprises a place holder 710 for inserting the actual pulse sequence or a part thereof to be executed. In this example, pulse sequence module 720 is inserted at the position of place holder 710 and the RF pulse for refocusing the MR response is calculated over the sequence defined through sequence module 720. In this example, sequence module 720 is cloned together with its subordinated hierarchy modules to the context of calculation sequence module 708, such that the RF pulse needed for the compensating sequence module 704 can be determined. In other words, sequence structure 700 allows for a generic determination of a RF pulse for refocusing, without necessary adaptations to the actual sequence. Although this example has been given in the context refocusing a MR response, also other physical models, peripheral nerve stimulation, gradient moments and the like can alternatively be described independent of the sequence and thus, likewise be used. For instance, in another example, an influence of eddy currents can be calculated and compensated for.

Figure 8:
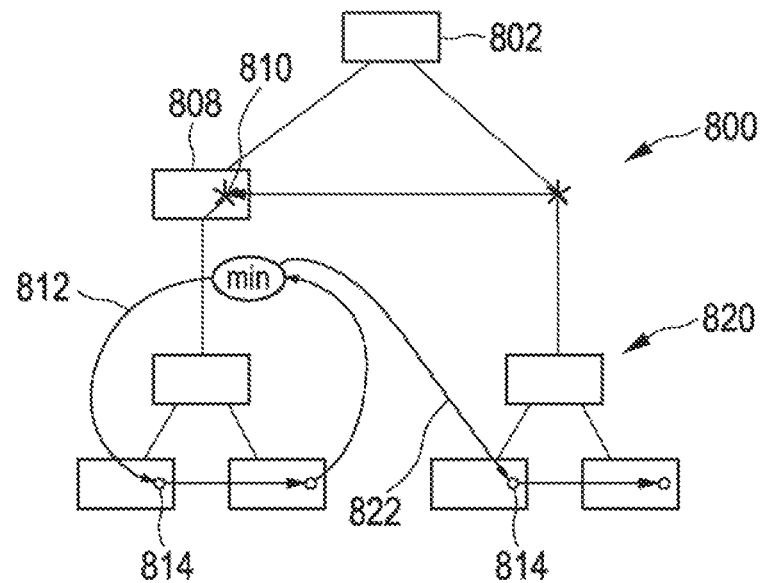
FIG. 8 schematically and exemplarily illustrates a structure hierarchy implementing parameter optimization.

FIG. 8 exemplarily and schematically shows an example of sequence structure 800, which implements an optimization routine as a further example of a versatile structure module. A root sequence module 802 defines a subordinated sequence module 808, which comprises a place holder 810 for inserting another sequence module including the dependent sequence hierarchy therein. Sequence module 808 defines an optimization routine 812 independent of the structural context. In this example, a sequence module 820 is inserted in the place holder 810 and the optimization routine 812 is executed on a cloned instance of sequence module 820. After optimization, parameter 814 has been optimized and an optimized parameter 822 is provided to the original sequence module 820.

Figure 9:
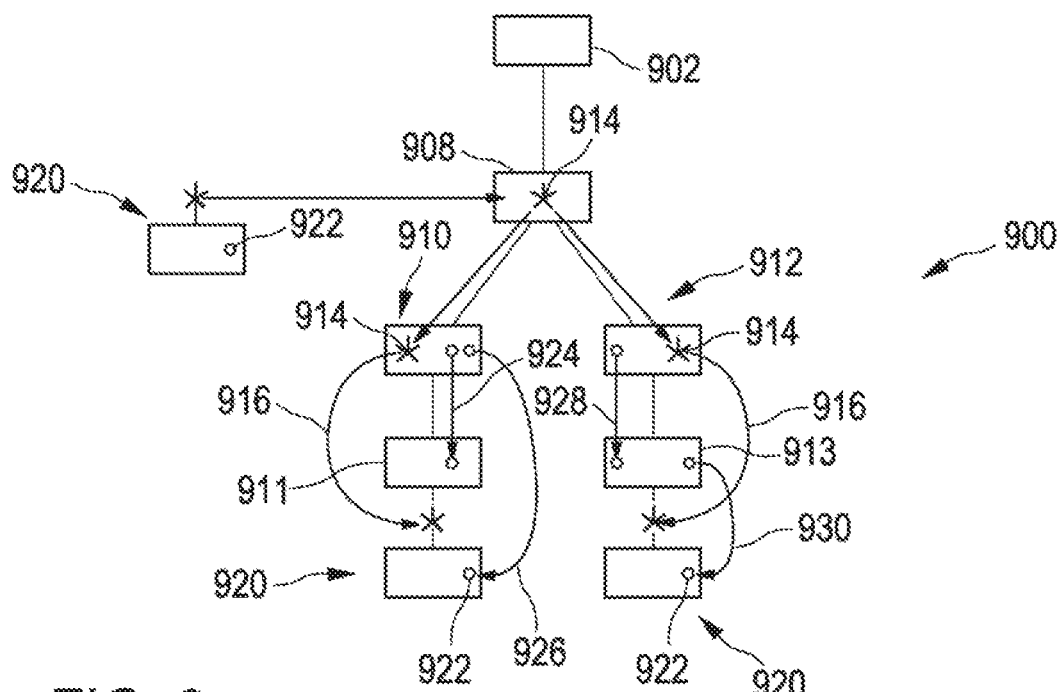
FIG. 9 schematically and exemplarily illustrates a structure hierarchy implementing structure operations.

FIG. 9 schematically and exemplarily illustrates a further example of a sequence structure 900 implementing structure operations. A root or main module 902 comprises sequence module 908 as hierarchically subordinated module. Sequence module 908 defines two subordinated loop structures 910 and 912. Sequence module 908 and both loop structures 910 and 912 comprise a placeholder 914, into which in this example a copy of sequence module 920 is inserted. Sequence module 920 comprises a dependency on parameter 922. Parameter 922 in this example is the amplitude of a gradient pulse, without being limited to the amplitude of a gradient pulse and can be different in a different example. Sequence module 920 is instantiated under loop module 911 and 913 for both loop structures 910, 912, respectively, as indicated with linking line 916. In this example, dummy loop 910 is executed 50 times, as defined by parameter 924. For each loop, sequence module 920 is executed at fixed amplitude 922, as indicated by line 926. In the actual measurement loop 912, loop module 913 is repeated for a number of times dependent on parameter 928, wherein the sequence module 920 receives values 930 for amplitude 922 dependent on the loop index. In this example, amplitude can thus be adapted for each respective row of the image. In summary, sequence structure 900 allows an implementation of a dummy cycle and a measurement loop independent of the structure of the source structure module.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfil the functions of several items recited in the claims. The mere fact that certain measures are recited in mutually different dependent claims does not indicate that a combination of these measures cannot be used to advantage.

The system 1 for determining at least part of a pulse sequence for acquiring imaging information using a magnetic resonance scanner in accordance with the method for determining at least part of a pulse sequence for acquiring imaging information using a magnetic resonance scanner can be implemented as program code means of a computer program and/or as dedicated hardware.

A computer program may be stored/distributed on a suitable medium, such as an optical storage medium or a solid-state medium or a tangible computer-readable medium, supplied together with or as part of other hardware, but may also be distributed in other forms, such as via the Internet or other wired or wireless telecommunication systems.

Any reference signs in the claims should not be construed as limiting the scope.

The invention claimed is:

1. A system for determining at least part of a pulse sequence for acquiring imaging information using a magnetic resonance scanner, the system comprising:
   a sequence module providing unit for providing sequence modules, wherein one or more sequence modules comprise a hierarchy description arranged for comprising one or more hierarchically subordinated sequence modules, and a parameter description arranged for comprising one or more parameter dependencies,
   a sequence hierarchy generating unit for generating a sequence hierarchy based on the sequence modules and the hierarchy description,
   a parameter dependency graph generating unit for generating a parameter dependency graph based on the parameter dependencies comprised in the parameter description of the sequence modules and based on the sequence hierarchy, and
   a parameter determination unit determining a parameter of the pulse sequence based on at least part of the parameter dependency graph.

2. The system of claim 1, further comprising:
   a pulse sequence instantiation unit for instantiating at least part of the pulse sequence based on at least part of the parameter dependency graph and at least part of the sequence hierarchy.

3. The system of claim 1 wherein the hierarchy description of one or more sequence modules is further arranged for comprising at least one structural operation description for defining a structural operation on the sequence hierarchy, wherein the sequence hierarchy generating unit is arranged for generating the sequence hierarchy further based on the at least one structural operation description in the sequence module.

4. The system of claim 1 wherein the hierarchy description is arranged for comprising hierarchically directly subordinated sequence modules and/or hierarchically subordinated sequence modules with one or more hierarchically intermediate sequence modules.

5. The system of claim 1 wherein the sequence module is arranged to define at least one hierarchically subordinated sequence module or a parameter dependency implicitly.

6. The system of claim 1 wherein the sequence module is further arranged to comprise an identifier for at least one of the hierarchically subordinated sequence modules in the hierarchy description.

7. The system of claim 1 wherein the sequence module is further arranged to comprise calculation instructions as part of the parameter description.

8. The system of claim 1 wherein the sequence hierarchy generating unit is arranged for generating the sequence hierarchy based on the sequence modules and the respectively comprised hierarchically subordinated sequence modules of the hierarchy description.

9. The system of claim 1 wherein the pulse sequence instantiation unit is arranged for combining the sequence hierarchy and the parameter dependency graph to a sequence parameter graph and for determining parameters from the resolved parameter dependencies within the sequence parameter graph.

10. The system of claim 1
wherein the sequence hierarchy generating unit is arranged to provide the sequence hierarchy as a directed tree structure; and/or
wherein the parameter dependency graph generating unit is arranged to provide the parameter dependencies graph as a directed acyclic graph.

11. A method for determining at least part of a pulse sequence for acquiring imaging information using a magnetic resonance scanner, the method comprising:
providing sequence modules, wherein one or more sequence modules comprise a hierarchy description arranged for comprising one or more hierarchically subordinated sequence modules, and a parameter description arranged for comprising one or more parameter dependencies;
generating a sequence hierarchy based on the sequence modules and the hierarchy description;
generating a parameter dependency graph based on the parameter dependencies comprised in the parameter description of the sequence modules and based on the sequence hierarchy; and
determining at least part of the pulse sequence based on at least part of the parameter dependency graph.

12. The method of claim 11, further comprising:
instantiating at least part of the pulse sequence based on the parameter dependency graph and the sequence hierarchy.

13. The method according to claim 11 wherein the sequence hierarchy is represented as a directed tree structure and wherein the parameter dependencies graph is represented as a directed acyclic graph.

14. A computer readable memory medium containing computer program instructions for controlling a computer processor, when executed, to determine at least part of a pulse sequence for acquiring imaging information using a magnetic resonance scanner, the computer program instructions causing a system as defined in claim 1 to carry out the method as defined in claim 11, when the computer program is executed.

15. A computer readable memory medium containing computer program instructions for controlling a computer processor, when executed, to drive or simulate magnetic resonance scanner, the computer program instructions causing a magnetic resonance scanner to execute at least part of a pulse sequence for acquiring imaging information by performing a method comprising:
receiving a sequence hierarchy comprising one or more sequence modules, wherein the sequence modules comprise a hierarchy description arranged for comprising one or more hierarchically subordinated sequence modules, and a parameter description arranged for comprising one or more parameter dependencies;
receiving a parameter dependency graph comprising parameters of the pulse sequence connected by parameter dependencies; and
executing at least part of the pulse sequence by calculating a parameter of the pulse sequence based on the parameter dependency graph.

* * * * *